US012712069B2

(12) United States Patent
Wilkening et al.

(10) Patent No.: US 12,712,069 B2
(45) Date of Patent: Aug. 18, 2026

(54) CONTROL METHOD AND CONTROL SYSTEM FOR REMOTE CONTROL OF A MEDICAL IMAGING SYSTEM

(71) Applicant: Siemens Healthineers AG, Forchheim (DE)

(72) Inventors: Wilko Wilkening, Erlangen (DE); Marco Leisegang, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 19 days.

(21) Appl. No.: 18/797,964

(22) Filed: Aug. 8, 2024

(65) Prior Publication Data

US 2025/0054610 A1 Feb. 13, 2025

(30) Foreign Application Priority Data

Aug. 11, 2023 (DE) ..................... 10 2023 207 782.5

(51) Int. Cl.
*G16H 40/67* (2018.01)
*A61B 90/00* (2016.01)
*G16H 30/20* (2018.01)
*G16H 30/40* (2018.01)
*G16H 40/40* (2018.01)

(52) U.S. Cl.
CPC ............. *G16H 30/40* (2018.01); *A61B 90/36* (2016.02); *G16H 30/20* (2018.01); *G16H 40/40* (2018.01); *G16H 40/67* (2018.01); *A61B 2090/371* (2016.02)

(58) Field of Classification Search
None
See application file for complete search history.

(56) References Cited

U.S. PATENT DOCUMENTS

2011/0137706 A1* 6/2011 Howard ............. G06Q 30/0246 705/7.29
2012/0191464 A1 7/2012 Chan et al.
2017/0270261 A1* 9/2017 Contolini ............... G16H 40/63
2019/0373237 A1* 12/2019 Limame ............... H04N 9/8715
2020/0389928 A1* 12/2020 Monson ................ H04W 72/04
2021/0049583 A1* 2/2021 Wurmfeld ............. G07F 19/206
2021/0209582 A1* 7/2021 Paliwal ................... G06F 21/31
2021/0220064 A1 7/2021 Kottenstette et al.
2021/0299376 A1* 9/2021 Gleim ................... H04W 4/023

* cited by examiner

*Primary Examiner* — John A Pauls
(74) *Attorney, Agent, or Firm* — Harness, Dickey & Pierce, P.L.C.

(57) ABSTRACT

One or more example embodiments relates to a control method for remote control of a medical imaging system comprising triggering a start signal in the remote control unit, to start an operation of the medical imaging system; capturing a number of items of optical information as at least one of images or light signals; verifying that the optical information comes from an examination area and has arrived at the remote control unit and, determining a capture time for the optical information if the optical information comes from the examination area and has arrived at the remote control unit; determining a start time at which the start signal was triggered or was sent to the medical imaging system; and comparing a time interval between the capture time and the start time with a specified comparison time interval.

20 Claims, 2 Drawing Sheets

I
S
12
Ts

II
K
B

III
?
Ta

IV
Ts
Ta
Tv

V

CONTROL METHOD AND CONTROL SYSTEM FOR REMOTE CONTROL OF A MEDICAL IMAGING SYSTEM

CROSS-REFERENCE TO RELATED APPLICATION(S)

The present application claims priority under 35 U.S.C. § 119 to German Patent Application No. 10 2023 207 782.5, filed Aug. 11, 2023, the entire contents of which is incorporated herein by reference.

FIELD

One or more example embodiments relates to a control method and a control system for remote control of a medical imaging system, and to a corresponding medical imaging system. For example, one or more example embodiments relates to remote controlled starting of an X-ray examination using a procedure of safe design.

RELATED ART

Many imaging methods, in particular those that use ionizing radiation, are not without risk. A particular problem is that, in any examination in which X-rays or indeed other radiation is used, the dose to which a patient and also any bystanders is exposed during the course of this examination should be as low as possible. In particular, it must be ensured that the patient is not incorrectly imaged and that protective devices, for example lead vests, do not slip. Consequently, at the start of an examination a patient or the examination area should be checked as to whether the patient is still correctly positioned, whether protective devices are still sitting true and whether the examination area is free of other humans.

It is therefore recommended that such imaging procedures are started using a remote control unit. This is currently implemented either by using a wired switch or an infrared remote control, which does not work if the direct path between the remote controller and the imaging system is blocked or too long. A visual connection may, for example, be ensured by using a comparatively short cable to connect a remote control to the imaging system, thereby forcing a user to remain in the vicinity of the examination area, so as to be able to monitor it.

SUMMARY

However, wired systems are also problematic because they are complicated and cables can get in the way or be damaged.

In particular in the case of mobile systems that can be used in a very wide variety of spaces, wired remote control systems or infrared remote control systems present a problem, in particular in small spaces in which the operator is supposed to stand outside the door or in large spaces in which the operator has no protective wall nearby and is thus exposed to radiation.

One or more example embodiments provides an alternative, more convenient control method and a corresponding control system for remote control of a medical imaging system with which the above-described disadvantages can be avoided and in particular an imaging system can be wirelessly remotely controlled.

This is achieved with a control method as claimed in claim 1, a control system as claimed in claim 10 and a medical imaging system as claimed in claim 13.

BRIEF DESCRIPTION OF THE DRAWINGS

One or more example embodiments are explained in detail below with reference to the appended figures. In the various figures, identical components are here provided with identical reference signs. The figures are not in general to scale. In the figures:

FIG. 1 shows a roughly schematic representation of a CT system with an exemplary embodiment of a control system according to the invention for carrying out the method.

DETAILED DESCRIPTION

Figure 2:
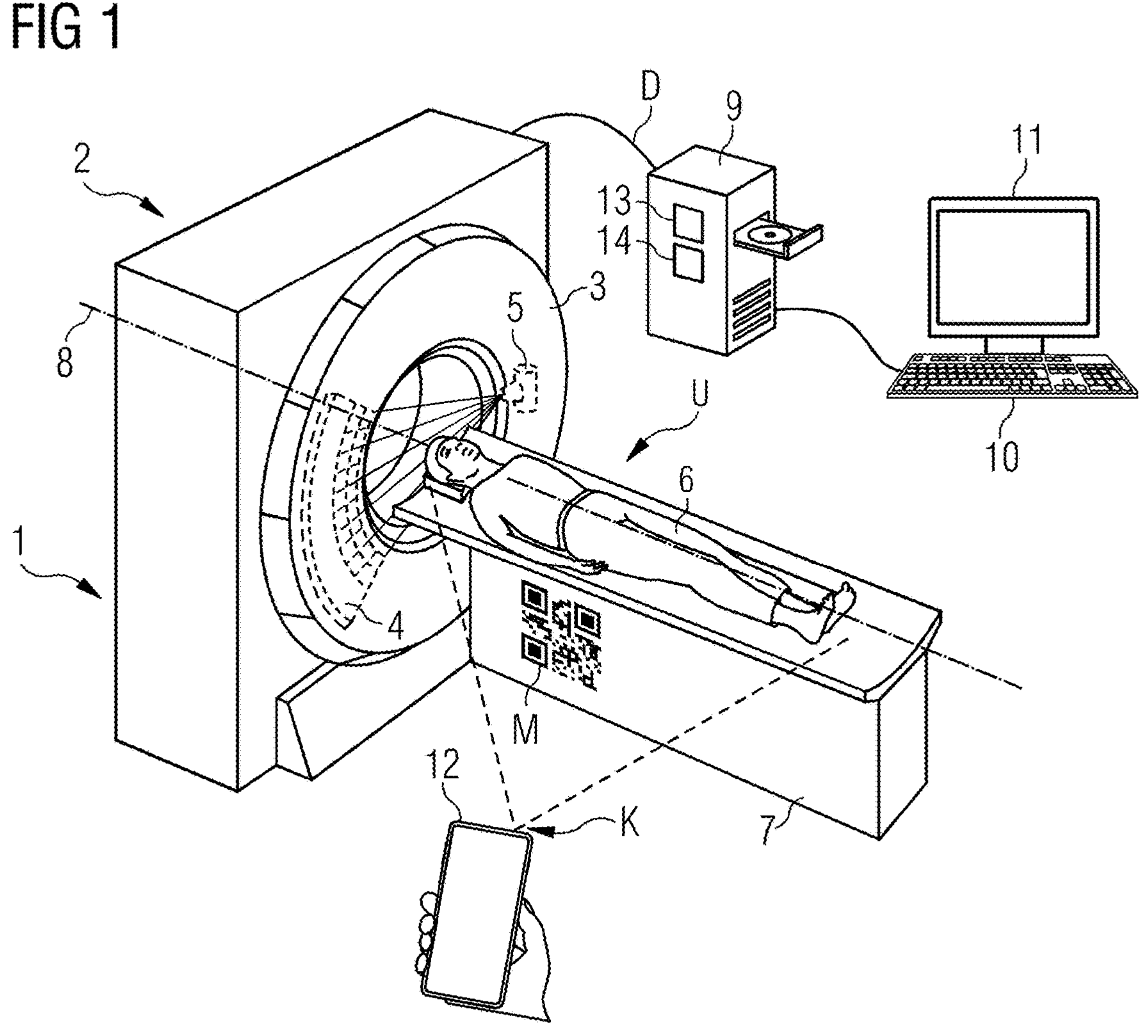
FIG. 2 shows a block circuit diagram of an exemplary embodiment of a method according to the invention.

A control method according to one or more example embodiments serves in remote control of a medical imaging system, for example a radiography system, a mammography system or a computed tomography system ("CT system"). Remote control proceeds using a start signal from a remote control unit, which is preferably transmitted wirelessly, in particular via a radio link. The control method comprises the following steps:

a) triggering a start signal in the remote control unit, to start an operation of the imaging system,
b) capturing a number of items of optical information in the form of images and/or light signals,
c) verifying that the optical information comes from the examination area and has arrived at the remote control unit and, if yes, determining a capture time for the optical information,
d) determining a start time at which the start signal was triggered or was sent to the imaging system,
e) comparing the time interval between the capture time and the start time with a specified comparison time interval, wherein an operation of the imaging system is only started by the start signal if the time interval lies within the comparison time interval.

Triggering a start signal in the remote control unit, to start an operation of the imaging system, fundamentally constitutes part of the prior art. An IR transmitter or a wired switch is currently frequently used for this purpose. In the prior art, however, the cable is sufficiently short always to ensure monitoring of the patient or of the examination area. One or more example embodiments is intended to ensure a high level of safety even with long cables and in particular with wireless remote control. The start signal is in this case preferably a radio signal. The remote control unit is in this case preferably connected to the imaging system by Bluetooth, WLAN or via the mobile radio network. The control system (i.e., fundamentally the remote control and imaging system or the control device thereof) is then designed to send a start signal from the remote control unit to the imaging system via this connection and there start an operation. The remote control unit is preferably a portable computer, in particular a smartphone, a tablet computer or a notebook.

The subsequent steps relate to making triggering of the operation of the imaging system particularly safe and in particular to ensuring that the examination area is also actually being monitored when the start signal is triggered.

It should be noted that the start signal does not as yet have to be transmitted by the remote control. Triggering may simply be achieved by a user triggering a start signal in the remote controller, for example by pressing a button. The start signal should arrive at the imaging system at the latest when the operation is to be started.

At least once the start signal has been triggered, the number of items of optical information in the form of images and/or light signals are captured. It would help understanding to imagine a camera capturing images, as light signals can also be identified in a video stream. In principle, however, a camera is not essential, rather all that is needed is a simple optical sensor on the remote control unit which can measure the brightness of an incident light beam.

It should be noted that this information can also be captured before the start signal is triggered and indeed thereafter. What is important here is that at least one of the items of information originates roughly from the time at which the start signal was triggered, as it has to be used to establish whether there was a visual connection to the examination area when the start signal was triggered. It is, of course, not essential for the information to come from the examination area, as the remote control unit, for example, may be held in any desired way by the user. However, no operation is started during the course of the method if there is no evidence of a visual connection to the examination area.

The information is captured, for example, by the remote control unit, preferably with a camera or, in the case of light signals, optionally also with another optical sensor. Alternatively, a number of images may be captured by an external camera, which then sends these images to the remote control unit. They have then to be displayed to the user by the remote control unit, so as to establish a visual connection by way of the displayed images.

With triggering of the start signal, the capture of information may in particular be started automatically or previously captured information may automatically be transmitted.

Once this information has been captured, it is verified that the optical information does indeed actually come from the examination area and has actually arrived at the remote control unit. It is thus important for the control method that the remote control unit is also involved in deciding whether a visual connection existed.

Theoretically, image analysis could be used to examine whether the examination area has indeed actually been imaged and, if yes, a signal could be sent by the remote control unit to indicate that it has received the image. There is a simpler way, however, involving examining whether the image depicts a specific marker unit which has been placed in the examination area. This point of verification can be embodied in diverse ways, as will be described in greater detail further below.

Common to each of these embodiments is that, if yes, i.e., if it could be verified that the optical information does indeed come from the examination area, the capture time of the optical information is determined. This time may, for example, be the time at which an image was produced or the start time of a video stream or of light signal capture.

The start time at which the start signal was triggered or transmitted to the imaging system is additionally also determined. This may take place at the same time as triggering of the start signal (i.e., in step a) or on receipt of the start signal at the imaging system. What is fundamentally important is simply that a time is established which correlates with the start signal or with the object thereof (namely to arrive at the imaging system and there optionally start an operation). The start time is preferably established on triggering of the start signal and data relating to this time is sent to where the subsequent comparison is carried out, for example to the imaging system.

The time interval between the capture time and the start time is then compared with a specified comparison time interval. This should not be too short (this would for example be of the order of microseconds or less), since otherwise start signals would frequently be ignored, but also not too long (for example of the order of minutes), so that it is possible to ensure that the visual connection was not simply produced too late, or too early and then discontinued. The range between $1/100$ s and 1 s is an advantageous comparison time interval. It is thus then, for example, looked at whether triggering of the start signal and capture of an image of the examination area took place within $1/10$ s.

An operation of the imaging system is in this case only started by a start signal if the time interval lies within the comparison time interval.

It should here be noted that it is definitely possible for verification of whether the examination area has been captured (see above), and this comparison with the comparison time interval to take place in the remote control unit. If the comparison was negative (i.e., verification failed or the time interval was too long), then the triggered start signal is simply not sent to the imaging system and the operation is thereby not started. In a method which is preferred in terms of practical application, both verification and comparison are performed in the control device of the imaging system.

A control system according to one or more example embodiments serves in remote control of a medical imaging system with a method according to one or more example embodiments. The control system comprises the following components:

- a remote control unit, designed for wireless transmission of a start signal for starting an operation of the imaging system,
- an optical capture system designed to capture a number of items of optical information in the form of images and/or light signals,
- a verification system, designed to verify that the optical information comes from the examination area and has arrived at the remote control unit and, if yes, determining a capture time for the optical information,
- a time stamp system, designed
- a) to determine a start time at which the start signal was triggered or was sent to the imaging system and
- b) to determine the capture time of the optical information, and
- c) to compare the time interval between the capture time and the start time with a specified comparison time interval, wherein the control system is designed such that an operation of the imaging system is only started by the start signal if the time interval lies within the comparison time interval.

The function of these components was already described above in relation to the control method.

A medical imaging system according to one or more example embodiments comprises a control system according to one or more example embodiments and/or is designed to perform a method according to one or more example embodiments.

A major part of the above-stated components of the system may be embodied, wholly or in part, in the form of software modules in a processor of a corresponding computer system, for example of a control system of a computed tomography system. A largely software-based embodiment has the advantage that computer systems which are already in service can also straightforwardly be retrofitted to operate in the manner according to one or more example embodiments via a software update. In this respect, the object is also achieved by a corresponding computer program product with a computer program which is directly loadable into a computer system, with program parts for carrying out the steps of the method according to one or more example embodiments, at least the steps that can be carried out by computer, when the program is executed in the computer system. It should be stated in this respect that the capture of spectral CT data in this case corresponds to the receipt of CT data, for example by a data bus or by reading out a memory unit. In addition to the computer program, such a computer program product can optionally comprise additional elements such as for example documentation and/or additional components including hardware components, such as for example hardware keys (dongles etc.) for using the software.

A computer-readable medium, for example a memory stick, hard disk or other transportable or permanently installed data storage medium on which are stored the program parts of the computer program which can be read in and executed by a computer system can be used for transport to the computer system or control device and/or for storage on or in the computer system or control device. The computer system can to this end have, for example, one or more cooperating microprocessors or the like.

It should be noted that in a computer system for the method the following method steps are carried out:

- recording a start signal in the remote control unit, to start an operation of the imaging system,
- outputting control commands for capturing a number of items of optical information in the form of images and/or light signals,
- verifying that the optical information comes from the examination area and has arrived at the remote control unit and, if yes, determining the capture time for the optical information,
- determining the start time at which the start signal was triggered or was sent to the imaging system,
- comparing the time interval between the capture time and the start time with a specified comparison time interval,
- outputting control commands for starting an operation of the imaging system, if the time interval lies within the comparison time interval on the basis of the start signal.

Further, particularly advantageous embodiments and developments of one or more example embodiments are revealed by the dependent claims and by the following description, wherein the claims of one category of claim may also be further developed in a manner similar to the claims and passages of the description relating to another category of claim and in particular individual features of different exemplary embodiments or variants may also be combined to form new exemplary embodiments or variants.

The verification system preferably comprises a marker unit. In particular, the imaging system here comprises a marker unit in or on the examination area. This marker unit is in particular an LCD unit, an LED unit or an e-paper unit, which is preferably arranged on the imaging system, in particular in the examination area thereof, and is designed to be captured by the camera. The marker unit may, for example, be mounted on a patient couch or a gantry of a CT apparatus.

The marker unit is preferably designed to display data in the form of a visually acquirable code and also displays this changing code at least at the capture time. This may for example be brought about by the marker unit beginning to send this code when the imaging system is switched on and stopping when the imaging system is switched off. It may however also only be switched on when the remote control unit transmits an activation signal. In a very simple embodiment, the marker unit is simply a QR code which is always visible on the imaging system. In this respect, however, it should be noted that the operation could then be started even if all that has happened is that a photo of the QR code has been captured.

The marker unit shows the code in particular as a character string, barcode or QR code and/or in the form of light signals, in particular on a modulated carrier frequency. Care should be taken to ensure that the code is easily visible and displayed on a large enough scale. Light signals could, for example, be transmitted by a simple LED, which is activated in particular by the remote control unit.

In the case of a changing code or of light signals, the start signal could be sent to the imaging system after it has been triggered in the remote control unit. There, however, it will not initially trigger the operation, but rather start display of the marker unit (for example the emission of a light signal or a changing code). Information about the code (and optionally also an image with this code) would then be sent by the remote control unit to the imaging system. On the basis of the information from the remote control unit, the start time (optionally arrival of the start signal at the imaging system) and capture time (derived from the code, for example) will then be compared and only then is it decided whether or not the operation should be started.

To verify that the optical information comes from the examination area, data relating to the marker unit is preferably looked for in the optical information. If this data is found, the time of capture is regarded as the capture time.

The marker unit is preferably designed to display data in the form of a constantly changing code. According to a preferred control method, the marker unit thus displays the data in the form of a constantly changing code. It is in this case preferable for the code to be configured in such a way that the capture time can be derived therefrom. This may for example take place in that the time is merely displayed (for example as a character string or QR code). It is, however, also possible for a counter to be started at a start time, since it is merely a question of a time interval between start time and capture time. The time interval is then compared on the basis of the code.

It is preferable for the code to change at a frequency greater than 1 Hz, in particular greater than 10 Hz (i.e. in a time interval shorter than 100 ms). This has the advantage of ensuring that the visual connection between remote control unit and imaging system arose close in time to triggering of the start signal.

As stated above, it may be advantageous for an activation signal to be transmitted by the remote control unit as first contact, and for a marker unit to be activated with this activation signal, with a start signal only then being sent by the remote control unit. The start signal may, however, also be understood as an activation signal.

According to a preferred control method, the optical information relating to the examination area comprises images which are captured using a camera on the remote control unit, on the imaging system or in an examination space of the imaging system. Verification that the images come from the examination area is then preferably achieved by establishing whether one of the number of images displays data from a marker unit or displays this marker unit itself.

A preferred control system, or the capture system thereof, thus comprises a camera. This is preferably arranged on the imaging system, or in an examination space in which the imaging system is located, or in or on the remote control unit.

In the preferred case of the camera being arranged in the remote control unit, a smartphone may, for example, be used as remote control unit. This would have fundamentally only to be in data contact with the control device of an imaging system and have an application with which a start signal can be sent, an image captured and this image analyzed or sent to the control device (for example together with the start signal).

In the preferred scenario of the camera being arranged outside the remote control unit, for example on the imaging system or in the examination area, it should be oriented and designed so as to send images of the examination area to the remote control unit. A camera on the imaging system or in the examination space is thus preferably set up to capture the examination area of the imaging system. The verification system is then designed to send the camera captures to the remote control unit, the remote control unit being designed to receive the sent captures and display them to a user.

The camera in the examination space or on the imaging system sends its images to the remote controller. Depiction of the images in the remote control unit (for example on the screen of a smartphone) produces a "visual connection". However, there is always the risk that the remote controller may show an out-of-date image (absent data link, image frozen), leading to the user taking a wrong decision. To avoid this, time stamps or other codes are preferably sent with the images (in particular with a marker unit with changing code). If the user activates the start signal, the code of the image displayed at that moment on the remote control unit is sent back to the imaging system with the start signal. The imaging system then checks with this code whether the image on the remote control unit was up-to-date. If not, the requested capture is refused. For the verification step, the data relating to the marker unit is preferably sent by the remote control unit to the imaging system or processed in the remote control unit.

According to one preferred control method, the capture time is derived from an on-line clock or from data relating to the marker unit.

According to one preferred control method, the start time is derived from a clock in the remote control unit and indicates when the start signal was triggered in the remote control unit. Alternatively, the start time is derived from a clock in the imaging system and indicates when the start signal was received by the imaging system.

In the event of images being sent to the remote control unit by the imaging system, it is preferable for these images to be sent to the remote control unit together with information about the respective capture time and for at least one item of information about such a capture time to be sent together with the start signal by the remote control unit to the imaging system.

According to one preferred control method, the time interval between the capture time and the start time is compared with a specified comparison time interval in the remote control unit. In the event of the time interval being longer than the comparison time interval, transmission of the start signal from the remote control unit to the imaging system is blocked. Alternatively or in addition, information may be sent to the imaging system that an operation of the imaging system is not to be started. This may serve to block the operation or for logging purposes.

According to one preferred control method, the time interval between the capture time and the start time is compared with a specified comparison time interval by the imaging system. In the event of the time interval being longer than the comparison time interval, an operation of the imaging system is not started, despite a start signal being present, at least until receipt of a new start signal together with a new comparison.

According to one preferred control method, an operation lasts for an operation time interval. Examples would be when a patient couch needs to be moved, or when a series of different captures is to be carried out. During this operation time interval, at least steps b) and c) (capture of the information and verification) are then run through repeatedly. Start of the operation proceeds as explained above, but it should be ensured that there is visual contact with the examination area throughout the operation time interval. Therefore, the operation is stopped if it can no longer be verified that the optical information comes from the examination area and has arrived at the remote control unit.

There are fundamentally two scenarios: the start signal starts the operation just once (until the end thereof or until it is stopped) or the start signal is sent continuously or repeatedly so as to carry on the operation.

In this case, steps a) to e) are preferably run through repeatedly, and the operation is stopped if a comparison reveals that the respective time interval lies outside the comparison time interval. It is preferable here that, before the operation is stopped, a warning is issued to a user, in particular by the remote control unit, and the operation is stopped only a predetermined time interval after the warning, with at least steps b) and c) being run through once again prior to stopping. This gives the user time to quickly re-establish visual contact.

According to one preferred control method, the start signal is a capture start signal. In this instance, image capture by the imaging system is started by a capture start signal only when the acquired time interval for this start signal is shorter than a specified comparison value.

According to one preferred control method, the start signal is an infusion start signal. In this instance, automatic infusion of a contrast agent by the imaging system is started by an infusion start signal only when the acquired time interval for this start signal is shorter than a specified comparison value.

According to one preferred control method, the start signal is a signal for moving a patient couch. In this case, a patient couch is started by the start signal only when the acquired time interval for this start signal is shorter than a specified comparison value.

According to one preferred control method, the remote control unit sends a code (a marker unit) captured using the camera together with the start signal. The time interval is then determined from the code sent with the start signal and the start time. The code is in this case preferably a QR code, which preferably changes at a frequency of greater than 10 Hz and the QR code captured using the camera is preferably sent together with the start signal. Alternatively, the imaging system comprises a light source, in particular a monochromatic light source, which is designed to send time data by modulating light signals, in particular at regular intervals.

One or more example embodiments has the advantage that, for example, X-ray image capture can be carried out using a cordless switch and thus cables, which are frequently in the way or can be damaged, can be dispensed with. Nonetheless, one or more example embodiments ensures that a patient is not exposed to unnecessary radiation, as a radiologist is able visually to verify positioning of the patient at the beginning of X-ray capture.

FIG. 1 shows an example of an imaging system in the form of a CT system 1 (computed tomography system) with a gantry 2 with a rotor 3. The rotor 3 comprises a radiation source 5 in the form of an X-ray source 5, and a radiation detector 4 configured to detect X-rays from the X-ray source. The CT system is just one of many possible systems in which use of one or more example embodiments would be advantageous. For example, it may also be used in mobile or stationary radiography systems.

The rotor 3 is rotatable about the axis of rotation 8. The patient 6 is placed on the patient couch 7 and can be moved through the gantry 2 along the axis of rotation 8. Computing unit 9 is provided to control the CT system 1 and to generate an image data set on the basis of signals detected by the radiation detector 4. Precisely how capture and reconstruction of images proceeds is known to a person skilled in the art and does not have to be described here.

The computing unit 9 here serves as a control device 9 for controlling the CT system 1. An input device 10 and an output device 11 are connected to this computing unit 9. The input device 10 and the output device 11 may, for example, enable user interaction or display of a image data set that has been produced.

To start capture, the examination area U should be checked, in particular with regard to whether the patient is correctly positioned and not at risk of excessive radiation exposure. This check has to be ensured even if the system is remote-controlled.

The control device 9 in this case therefore also comprises components of a control system according to one or more example embodiments for remote control of the medical imaging system 1 using a method as depicted, for example, in FIG. 2, namely a verification system 13 and time stamp system 14.

The control system comprises overall a remote control unit 12, here in the form of a smartphone 12, a capture system K, here in the form of camera K of smartphone 12, said verification system 13 and a time stamp system 14.

The remote control unit 12 is here designed for wireless transmission of a start signal S for starting an operation of the imaging system 1, for example image acquisition thereby. To this end, the start signal S may, for example, be sent by Bluetooth, WLAN or a mobile radio network from the smartphone 12 to the imaging system 1 and there start an operation, provided it is not blocked.

The optical capture system K used in this example is camera K of smartphone T. Dashed lines indicate the area which camera K captures as optical information B, here in the form of images B. The images B may serve as evidence that a visual connection is present or indeed as that visual connection itself, as will be described in greater detail below.

A marker unit M is apparent on the patient couch 7, said unit here being captured as part of image B. The marker unit shown here is a QR code. This QR code does not necessarily have to be static. Indeed, it is advantageous for it to change (rapidly) and for this change to be interpreted as time information. Instead of the QR code, a light source could very well also emit light signals in the form of information modulated to a carrier frequency, which information is then captured in a video stream of the camera (or by a simple photosensor) and interpreted or decoded therefrom.

The verification system 13 then verifies whether or not the optical information comes from the examination area. In this example the verification system 13 is running as a software module on the computing unit 9. The images B captured by camera K are thus sent to the computing unit, in particular together with the start signal S. For verification purposes, it is then possible, for example, to check whether the marker unit M is visible in the transmitted images. Since the images come from the remote control unit 12, it is also certain that the optical information B has arrived at this unit. It may thus be assumed in the instance depicted that the verification was positive.

The capture time Ta of the images B is then determined. This may be done using the clock on the smartphone 12. It should here be noted, however, that a photo of a (static) QR code could theoretically have been captured which was held in front of the camera, or the clock of the smartphone 12 could be wrong. To rule these possibilities out, a dynamic QR code is advantageous, which for example sends time information which is accurate to the second. Since all that is important here is a time interval, and the start time may also be seen from arrival of the start signal S at the imaging system 1, this time information may very well be relative time information relating to any timer of the imaging system 1.

If a user selects a start signal S in the smartphone 12, an image B is also captured with camera K, which should be directed at the examination area U (for verification purposes). This image B may then be sent to the control device 9 together with the start signal S.

When this start signal S arrives at the control device 9, the start time Ts is established on the basis of a timer of the time stamp system 14. The capture time Ta is then established from the transmitted image (in particular the QR code). This should roughly match the start time, since the start signal S and image capture proceeded virtually simultaneously. It is then thus simply possible to compare the time interval between the capture time Ta and the start time Ts with a specified comparison time interval, for example 1 s.

If this time interval is shorter, the desired operation of the imaging system 1 is started by the start signal S, but not if it is longer.

FIG. 2 is a further illustration, as a block diagram, of a control method according to one or more example embodiments for remote control of a medical imaging system 1 (see for example FIG. 1) using a start signal S from a remote control unit 12.

In step I of this example, a start signal S is triggered in the remote control unit 12 (here once again a smartphone 12). This start signal S serves, as described above, to start an operation of the imaging system 1, for example image capture. At the same time as the start signal S is triggered, a start time Ts is established, here on the basis of the internal clock of the smartphone 12.

In step II, a capture system K, for example the camera K, of the smartphone 12 is then used to capture an image B. This may take place automatically on triggering of the start signal S. As is apparent, the camera K was directed at the examination area U and shows an image B, in which the patient P and the marker unit M are visible. In this example it is important for the camera K also to be directed deliberately at the examination area U, so as to indicate that there is a visual connection. Instead of image B, a light signal could theoretically also be captured. It is also possible for the image B to be captured by a camera K in the examination space U, as outlined in FIG. 3. What is important is that the examination area U can in some way be seen by the operator of the remote control unit 12 and that this is also evidenced by the capture (the optical information B).

In step III it is then verified that the image B (or the optical information B) comes from the examination area U and has arrived at the remote control unit 12. This may proceed here as described above by the verification system 13 reading out the QR code. The capture time Ta of the image B is then established. This may take place, for example, by the smartphone 12 also sending the time of capture. It is safer, however, for the capture time Ta, as already described above, to be derived from a changing QR code of the marker unit M.

In step IV, the time interval between the capture time Ta and the start time Ts is compared with a specified comparison time interval Tv. This is intended to ensure that not too much time has elapsed between the identified visual contact and triggering of the start signal S, i.e., basically that visual contact existed during triggering of the start signal S.

In step V, an operation of the imaging system is started by the start signal S if the time interval lies within the comparison time interval and is not started if not.

This operation may theoretically also take place in the remote control unit 12, the start signal S being sent to the imaging system in the final step if the time interval lies within the comparison time interval and not being sent if it does not.

Figure 3:
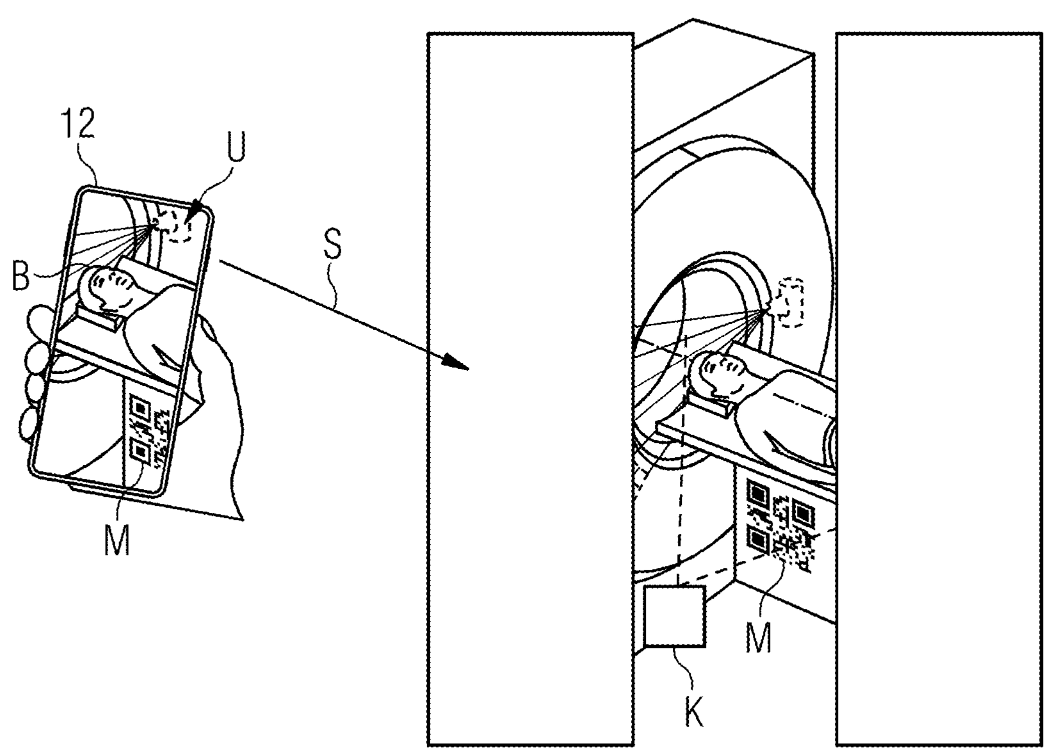
FIG. 3 shows an outline of the procedure.

FIG. 3 shows a scenario in which there is no direct line of sight between the remote control unit 12 and the examination area U, for example because the examination space is too small or the operator has to stand outside a closed door for reasons of radiation protection. Here a camera K in the examination space captures the examination area U and sends the captured images B to the remote control unit 12. The captured images B are then displayed on a display of the remote control unit 12 and in this way constitute a visual connection. The method according to FIG. 2 may also be carried out in this way, and verification may produce a positive result with this visual connection.

It should finally once again be noted that the figures described in detail above merely depict exemplary embodiments which can be modified in the most varied manner by a person skilled in the art without departing from the scope of the invention. Furthermore, use of the indefinite article "a" does not rule out the possibility of a plurality of the features in question also being present. Likewise, the terms "unit" and "apparatus" do not rule out the possibility of the components in question consisting of a plurality of interacting sub-components which may optionally also be spatially distributed. The expression "a number" should be understood to mean "at least one". Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions operations illustrated as being performed serially in two consecutive blocks may actually be performed simultaneously, cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in art the effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as carrier wave); the term computer-readable medium is on a therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A control method for remote control of a medical imaging system using a start signal from a remote control unit, the method comprising:
 triggering the start signal in the remote control unit, to start an operation of the medical imaging system;
 capturing a number of items of optical information as at least one of images or light signals;
 verifying that the optical information comes from an examination area and has arrived at the remote control unit;
 determining a capture time for the optical information in response to verifying that the optical information comes from the examination area and has arrived at the remote control unit;
 determining a start time at which the start signal was triggered or was sent to the medical imaging system;
 comparing a time interval between the capture time and the start time with a specified comparison time interval; and
 starting the operation of the medical imaging system in response to the time interval being within the specified comparison time interval.

2. The control method of claim 1, wherein
 the medical imaging system comprises a marker unit in or on the examination area, the marker unit displaying data as a visually acquirable code, and
 the verifying includes looking for data relating to the marker unit in the optical information and regarding a time of capture as the capture time in response to the data relating to the marker unit being found.

3. The control method of claim 2, wherein
 the marker unit displays the data as a constantly changing code, from which the capture time can be derived, and comparison of the time interval between the capture time and the start time with the specified comparison time interval is based on the constantly changing code.

4. The control method of claim 3, wherein the constantly changing code changes at a frequency greater than 1 Hz and an activation signal is transmitted by the remote control unit as a first contact, and the marker unit is activated with the activation signal.

5. The control method of claim 2, wherein the marker unit displays data as at least one of a character string, a barcode, a QR code or light signals.

6. The control method of claim 1, wherein
 the optical information from the examination area comprises images which are captured using a camera on the remote control unit, on the medical imaging system or in an examination space of the medical imaging system; and
 the verifying that the optical information comes from the examination area is achieved by determining whether one of the number of items of optical information displays data relating to a marker unit or displays the marker unit.

7. The control method of claim 6, wherein
 the camera is arranged
  in the remote control unit, or
  outside the remote control unit, and sends images of the examination area to the remote control unit; and
 one of
  the data relating to the marker unit is sent by the remote control unit to the medical imaging system for the verifying that the optical information comes from the examination area, or the data relating to the marker unit is processed in the remote control unit.

8. The control method of claim 1, wherein at least one of the capture time is derived from an online clock or from data relating to a marker unit, the start time is derived from a clock in the remote control unit and indicates when the start signal was triggered in the remote control unit, or the start time is derived from a clock in the medical imaging system and indicates when the start signal was received by the medical imaging system.

9. The control method of claim 8, wherein, if images are sent to the remote control unit by the medical imaging system, the images are sent to the remote control unit with information about the capture time and at least one item of information about the capture time is sent to the medical imaging system by the remote control unit together with the start signal.

10. The control method of claim 1, wherein at least one of in the remote control unit and, if the time interval between the capture time and the start time is longer than the specified comparison time interval, transmission of the start signal from the remote control unit to the medical imaging system is at least one of blocked or information is sent to the medical imaging system that the operation of the medical imaging system is not to be started, or by the medical imaging system and, if the time interval between the capture time and the start time is longer than the specified comparison time interval, the operation of the medical imaging system is not started at least until a new start signal together with a new comparison is received.

11. The control method of claim 1, wherein the operation lasts for an operation time interval and during the operation time interval at least steps capturing and verifying are repeated, and the operation is stopped if the optical information coming from the examination area cannot be verified and has arrived at the remote control unit.

12. The control method of claim 11, wherein the start signal starts the operation only once, and the start signal is sent continuously or repeatedly to continue the operation.

13. The control method of claim 1, wherein the start signal is a capture start signal, and image capture by the medical imaging system being started by the capture start signal when the time interval between the capture time and the start time is shorter than the specified comparison time interval; or an infusion start signal, automatic infusion of a contrast agent by the medical imaging system is started by the infusion start signal when the time interval between the capture time and the start time is shorter than the specified comparison time interval.

14. The control method of claim 1, wherein the remote control unit sends a code captured using a camera with the start signal, and the time interval between the capture time and the start time is determined from the code sent with the start signal and the start time.

15. A control system configured to perform the method of claim 1, the control system comprising:

the remote control unit;

an optical capture system configured to capture the number of items of optical information;

a verification system configured to perform the verifying; and a time stamp system configured to perform the determining and the comparing.

16. The control system of claim 15, wherein the optical capture system includes a camera on the medical imaging system, in an examination space in which the medical imaging system is located, or on the remote control unit.

17. The control system of claim 15, wherein the verification system comprises a marker unit, an LED unit or an e-paper unit, on the medical imaging system.

18. A medical imaging system, comprising the control system of claim 15.

19. A non-transitory computer program product comprising commands which, when executed by a computer, cause the computer to perform:

recording a start signal in a remote control unit to start an operation of a medical imaging system;

outputting control commands for capturing a number of items of optical information as at least one of images or light signals;

verifying that the optical information comes from an examination area and has arrived at the remote control unit;

determining a capture time for the optical information if in response to verifying that the optical information comes from the examination area and has arrived at the remote control unit;

determining a start time at which the start signal was triggered or was sent to the medical imaging system;

comparing a time interval between the capture time and the start time with a specified comparison time interval; and outputting control commands for starting the operation of the medical imaging system in response to the time interval being within the specified comparison time interval.

20. A non-transitory computer-readable storage medium comprising commands which, when executed by a computer, cause the computer to perform:

recording a start signal in a remote control unit, to start an operation of a medical imaging system;

outputting control commands for capturing a number of items of optical information as at least one of images or light signals;

verifying that the optical information comes from an examination area and has arrived at the remote control unit;

determining a capture time for the optical information in response to verifying that the optical information comes from the examination area and has arrived at the remote control unit;

determining a start time at which the start signal was triggered or was sent to the medical imaging system;

comparing a time interval between the capture time and the start time with a specified comparison time interval; and outputting control commands for starting an operation of the medical imaging system in response to the time interval being within the specified comparison time interval.

* * * * *